(12) United States Patent
Tseng et al.

(10) Patent No.: US 7,705,301 B2
(45) Date of Patent: Apr. 27, 2010

(54) ELECTRON BEAM APPARATUS TO COLLECT SIDE-VIEW AND/OR PLANE-VIEW IMAGE WITH IN-LENS SECTIONAL DETECTOR

(75) Inventors: Chi-Hua Tseng, Jubei (TW); Zhong-Wei Chen, San Jose, CA (US); Xuedong Liu, Sunnyvale, CA (US)

(73) Assignee: Hermes Microvision, Inc., Hsin-Chu (TW)

(*) Notice: Subject to any disclaimer, the term of this patent is extended or adjusted under 35 U.S.C. 154(b) by 304 days.

(21) Appl. No.: 11/755,705

(22) Filed: May 30, 2007

(65) Prior Publication Data

US 2008/0006771 A1 Jan. 10, 2008

Related U.S. Application Data

(60) Provisional application No. 60/819,057, filed on Jul. 7, 2006.

(51) Int. Cl.
*G01N 23/00* (2006.01)
*G21K 7/00* (2006.01)

(52) U.S. Cl. .............. 250/310; 250/311; 250/306; 250/307; 250/396 ML; 250/442.11; 250/492.1; 324/751; 324/765

(58) Field of Classification Search ........ 250/310, 250/311, 306, 307, 396 ML, 442.11, 492.1; 324/751, 765
See application file for complete search history.

(56) References Cited

U.S. PATENT DOCUMENTS

| | | | |
|---|---|---|---|
| 4,149,074 A | 4/1979 | Schliepe et al. | |
| 4,438,332 A | 3/1984 | Lichtenegger | |
| 4,658,137 A | 4/1987 | Garth et al. | |
| 4,831,266 A | 5/1989 | Frosien et al. | |
| 6,545,277 B1 | 4/2003 | Kella et al. | |
| 6,646,261 B2 | 11/2003 | Krans | |
| 6,707,041 B2 | 3/2004 | Essers | |
| 6,777,675 B2 | 8/2004 | Parker et al. | |
| 7,141,791 B2 * | 11/2006 | Masnaghetti et al. | 250/311 |

\* cited by examiner

*Primary Examiner*—Nikita Wells
*Assistant Examiner*—Meenakshi S Sahu
(74) *Attorney, Agent, or Firm*—Sawyer Law Group, P.C.

(57) ABSTRACT

An electron beam apparatus and method are presented for collecting side-view and plane-view SEM imagery. The electron beam apparatus includes an electron source, some intermediate lenses if needed, an objective lens and an in-lens sectional detector. The electron source will provide an electron beam. The intermediate lenses focus the electron beam further. The objective lens is a combination of an immersion magnetic lens and a retarding electrostatic lens focuses the electron beam onto the specimen surface. The in-lens detector will be divided into two or more sections to collect secondary electrons emanating from the specimen with different azimuth and polar angle so that side-view SEM imagery can be obtained.

15 Claims, 11 Drawing Sheets

ELECTRON BEAM APPARATUS TO COLLECT SIDE-VIEW AND/OR PLANE-VIEW IMAGE WITH IN-LENS SECTIONAL DETECTOR

CROSS-REFERENCE TO RELATED APPLICATIONS

This application claims the benefit of priority to U.S. Provisional Application No. 60/819,057, filed Jul. 7, 2006, and entitled, "Electron Beam Apparatus To Collect Side-View and/or Plane-View Image With In-Lens Sectional Detector", all of which is incorporated herein by reference.

BACKGROUND OF THE INVENTION

The present invention is related generally to scanning electron microscopes and more particularly to a system and method to collect the side-view and plane-view SEM image.

DESCRIPTION OF THE RELATED ART

A low-landing energy, high resolution SEM (scanning electron microscope) with the capability of capturing a side-view and plane-view image is a very important metrology tool to inspect and review defects in a semiconductor wafer. This SEM accelerates the new wafer processing technology ramp and improves the yield during mass production. For the conventional SEM with capability of collecting side-view SEM image of specimen, one or more side-detectors are placed very close to the specimen surface. The objective magnetic lens usually has a conical shape to make space for the side detectors. The space between the specimen surface and the lens pole-piece has no or very weak axial magnetic field and electrostatic field so that the secondary electrons emanating from the specimen with a polar angle can be collected by the side-detector. In order to improve the collection efficiency, a positive voltage with respect to the specimen will be applied to the side-detector to attract the secondary electron signal. This conventional SEM layout has a poor aberration property, and it is difficult to achieve high resolution, especially for low landing energy SEM imaging. It is known that the combination of immersion magnetic lens and retarding electrostatic lens has very low aberration coefficients and can achieve high resolution for the low landing energy. Due to strong axial magnetic field and extraction electric field between the specimen surface and lens pole-piece of this compound lens, the layout of the side-detector near the specimen surface to collect the side-view SEM image cannot work anymore. The presented invention will solve the conflict between high-resolution achieving and side-view imaging for low landing energy SEM.

SUMMARY OF THE PRESENT INVENTION

An object of the present invention is to provide an apparatus and method to collect the secondary electrons emanating from specimen surface without influencing the primary electron beam thereafter form side-view and/or plane-view image of a high resolution and low landing energy SEM.

This and other objects are achieved in an electron detector structure and aperture arrangement around the primary beam optical axis to capture the secondary and backscattered electrons emanating from specimen surface with different azimuth and polar angles.

In one embodiment, an apparatus for generating side-view and plane-view image from a specimen is disclosed. The apparatus includes a charged particle beam generator arranged to generate and control a charged particle beam substantially towards a portion of the specimen and a detector arranged to detect charged particles emanating from the specimen to allow generation of an image of interested portion of the specimen.

In another embodiment, a charge particle detector for obtaining an image of a portion of specimen surface is disclosed. An in-lens sectional detector composed of at least two segments with an aperture is arranged to capture secondary electrons and backscattered electrons emanating from specimen surface with different azimuth and polar angles. For further embodiment, an ExB filter is positioned to guide the secondary electrons and backscattered electrons emanating from specimen surface substantially toward the off-axis sectional detector.

In yet another embodiment, a detector for generating quality side-view image is disclosed. An aperture on the detector with 3 millimeters diameter is calculated for quality side-view image and image aberration.

BRIEF DESCRIPTION OF THE DRAWINGS

The present invention will be readily understood by the following detailed description in conjunction with the accompanying drawings, wherein like reference numerals designate like structural elements, and in which.

DESCRIPTION OF THE PREFERRED EMBODIMENTS

Reference will now be made in detail to specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a through understanding of the present invention. The present invention may be practiced without some or all of these specific details. In other instances, well known process operations have not been described in detail in order not to unnecessarily obscure the present invention.

Figure 1:
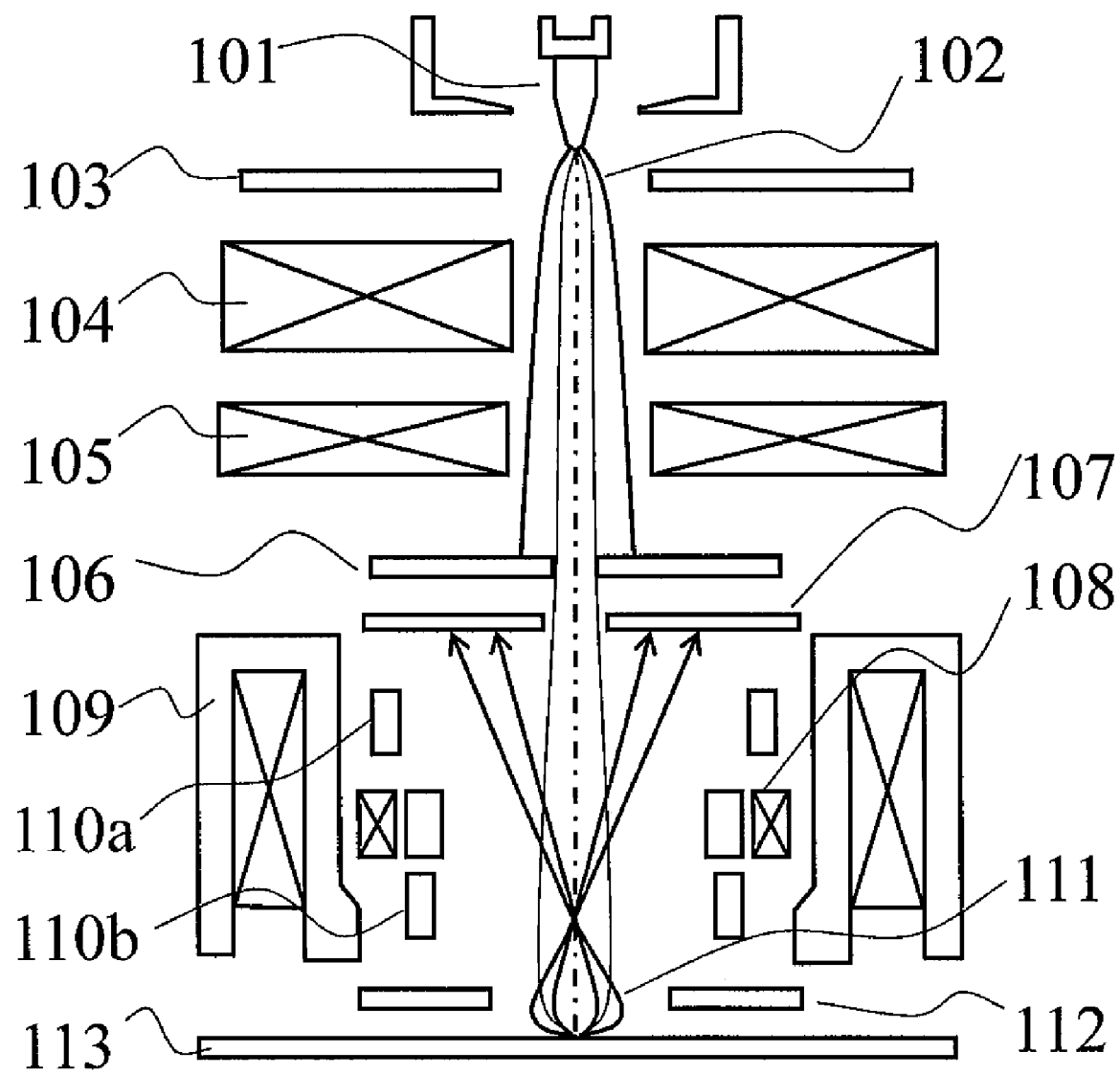
FIG. 1 is a diagrammatic representation of schematic drawing of the electron beam apparatus.

The present invention may be implemented within any suitable measurement device that detects charged particles towards a sample and then detects emitted particles from the sample. FIG. 1 is a diagrammatic representation of an electron beam apparatus 100 (SEM) in accordance with one embodiment of the present invention. The SEM system 100 includes an electron beam generator (101 through 112) that generates and directs an electron beam 102 substantially toward an area of interest on a specimen 113.

The SEM system 100 includes an electron beam gun tip 101 for providing the electron beam to an anode 102 to create an electron field. Gun lenses 104 and 105 retain the electric field. A blanking plate 106 retains the electron beam shape. The SEM system 100 also includes an in-lens sectional detector 107 arranged to detect charged particles 111 (secondary electrons SE and/or backscattered electrons BSE) emanating from the specimen surface 113.

The SEM system 100 includes deflectors 108 and 110 to deflect the electric field. The SEM system also includes a bottom seal 112 for holding the assembly. The SEM system 100 includes an objective lens 109 which provides a magnetic immersion function and an electrostatic retarding function. The SEM system 100 also includes an image generator (not shown) for forming an image from the emanated particles. The electron beam generator and sectional detector are further described below, along with other features of the SEM system 100.

Figure 2:
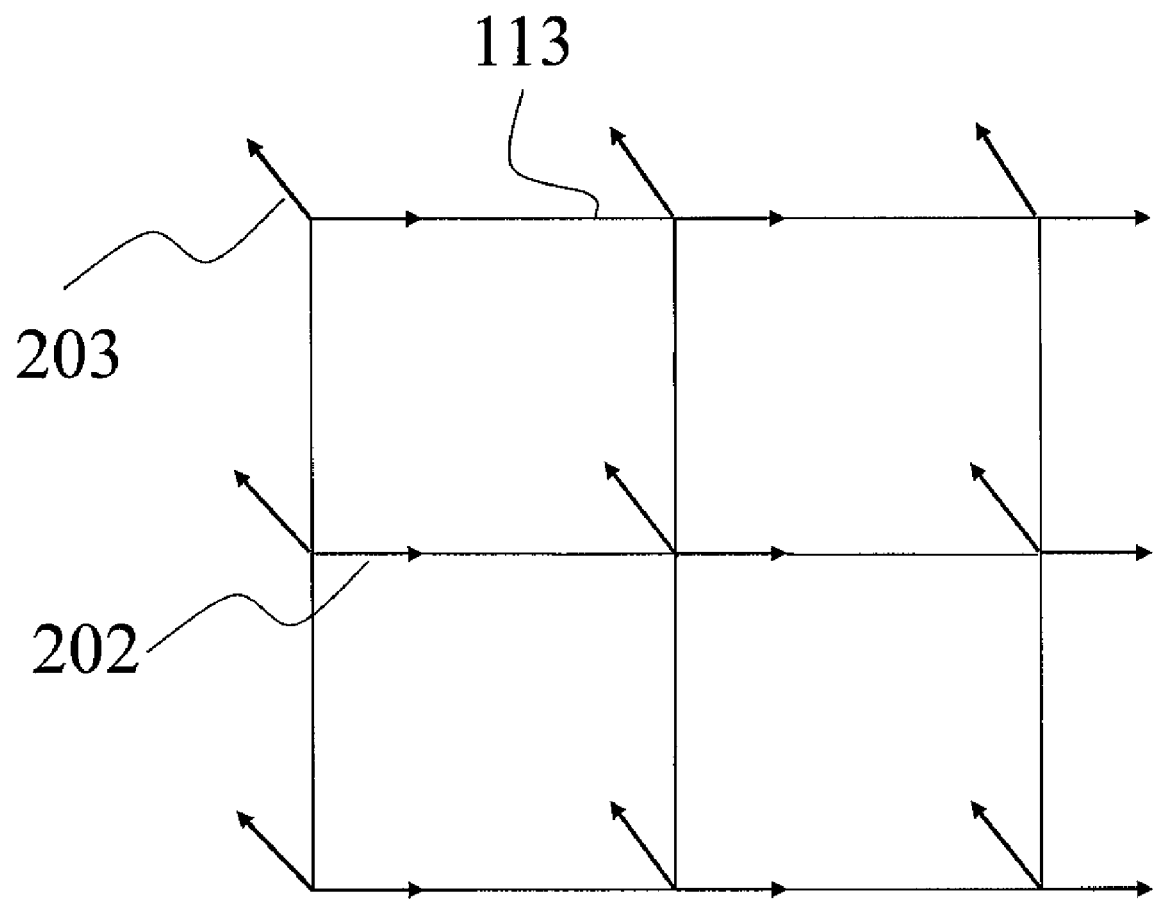
FIG. 2 is a diagrammatic representation of the emanating secondary electrons from specimen surface with azimuth angle of 0 degree and 135 degree.
Figure 3:
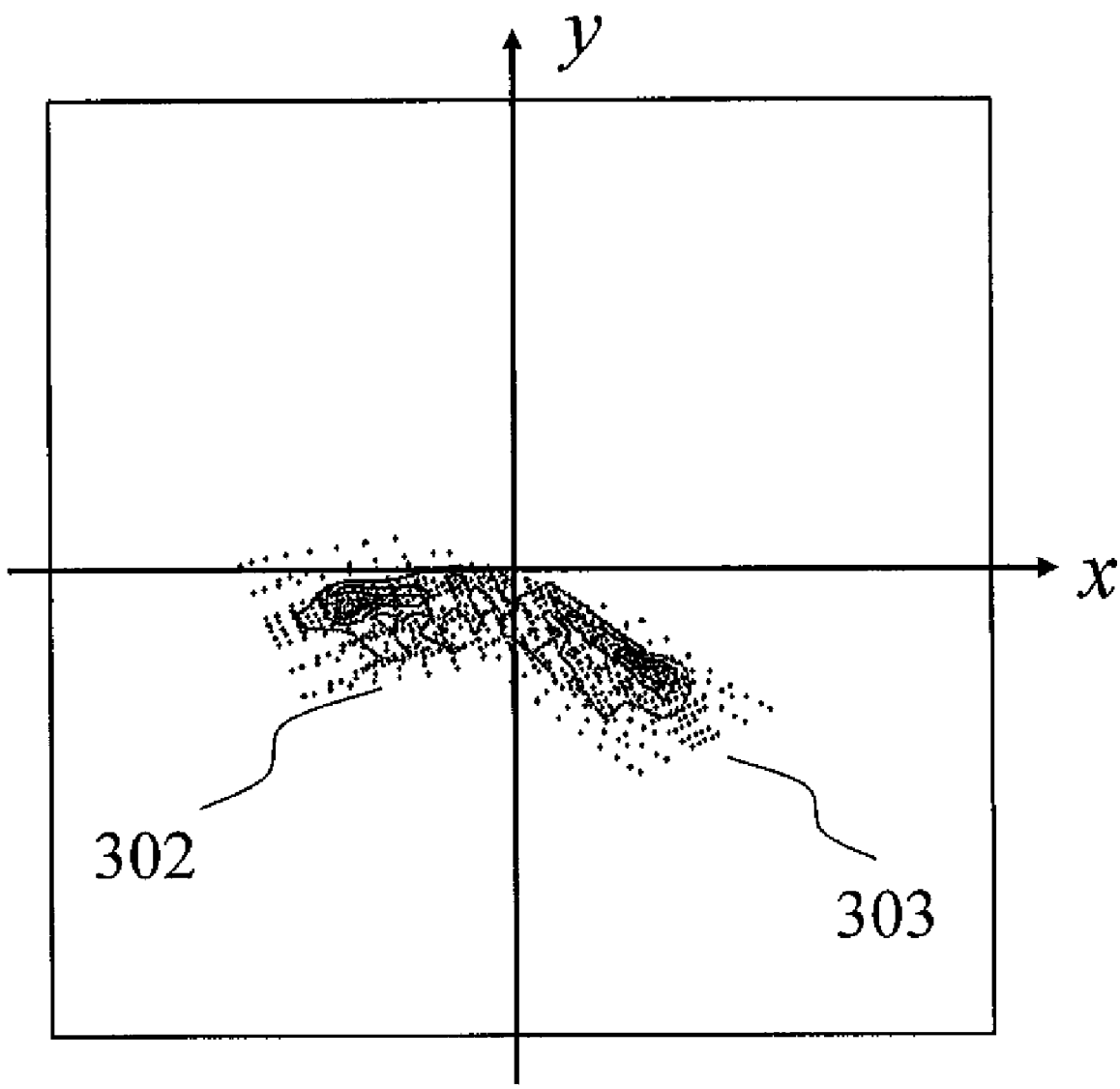
FIG. 3 is the corresponding distribution of the secondary electrons emanating from specimen surface with azimuth angle of 0 degree, 135 degree and different polar angle when they arrive at the detector plane.

The landing location of these charged particles when they arrive at the detector plane is determined by their initial energy and escaping angle emanating from the specimen surface. FIG. 2 is a diagrammatic representation of electron trajectory simulation of the emanating SE from specimen surface 113 with initial trajectory condition of azimuth angle 0 degree 202 and 135 degree 203. The corresponding landing position image on the detector plane is illustrated on FIG. 3. 302 is the landing area for SE from specimen surface 113 with 0 degree azimuth angle and 303 is the landing area for SE from specimen surface 113 with 135 degree azimuth angle.

Figure 4:
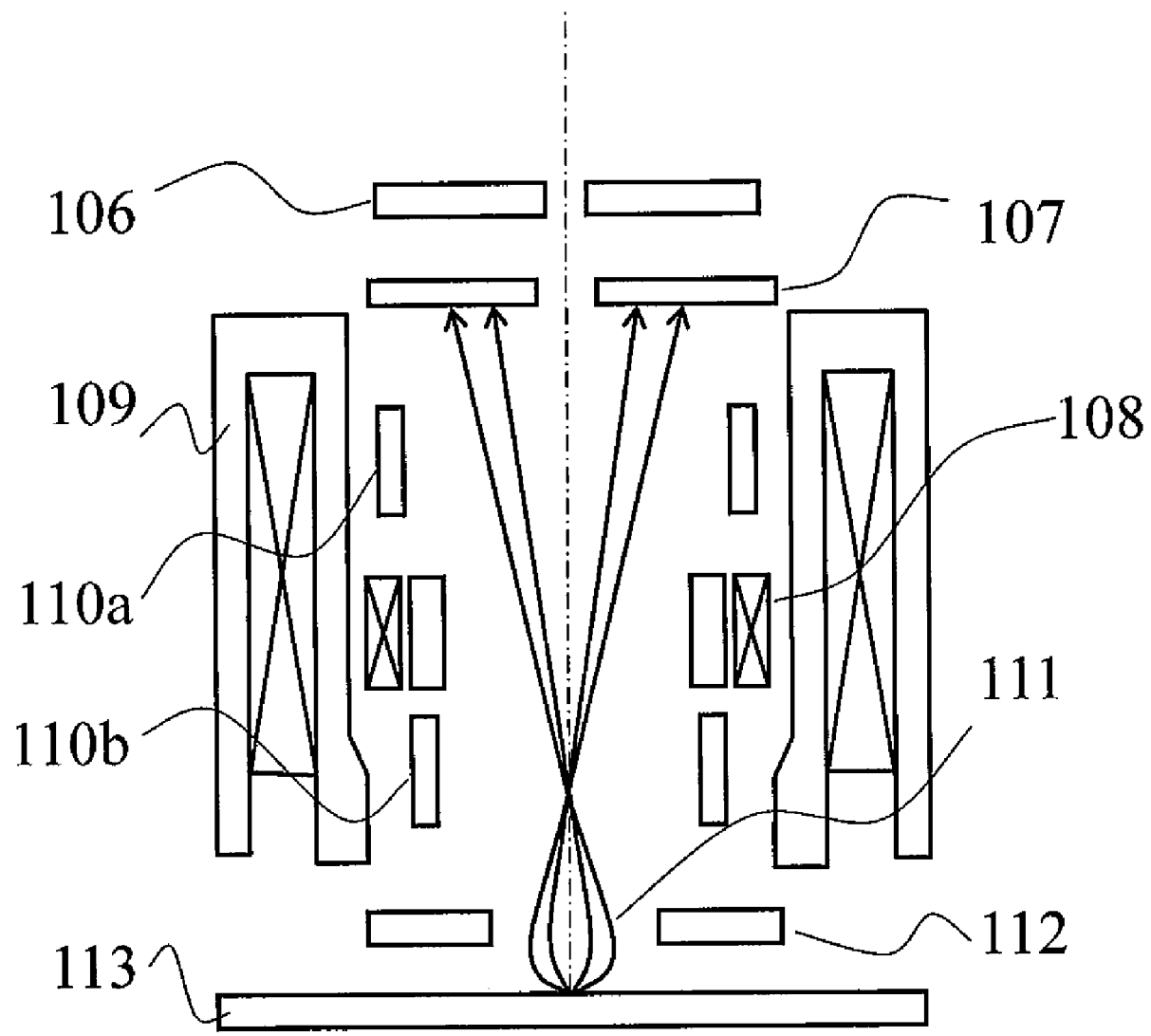
FIG. 4 is a diagrammatic representation of the trajectory of secondary electrons emanating from specimen surface to sectional detector without any other electronic and magnetic field affection except the objective lens field.

FIG. 4 is a diagrammatic representation of the trajectory of SE emanating from specimen surface 113 to in-lens sectional detector 107 without any other electronic and magnetic field affection except the objective lens field.

Figure 6:
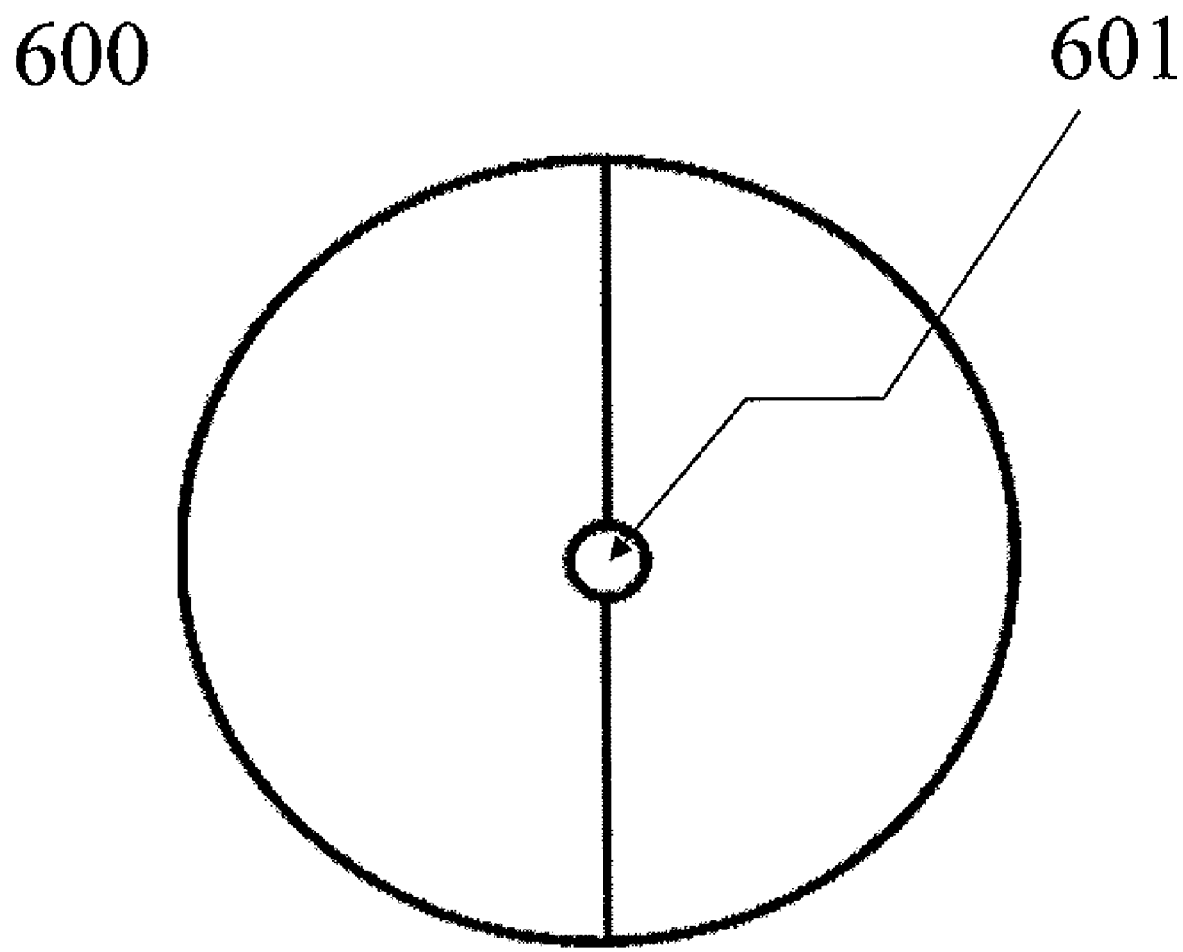
FIG. 6 is a diagrammatic representation of a sample sectional detector with an aperture in the center.
Figure 7:
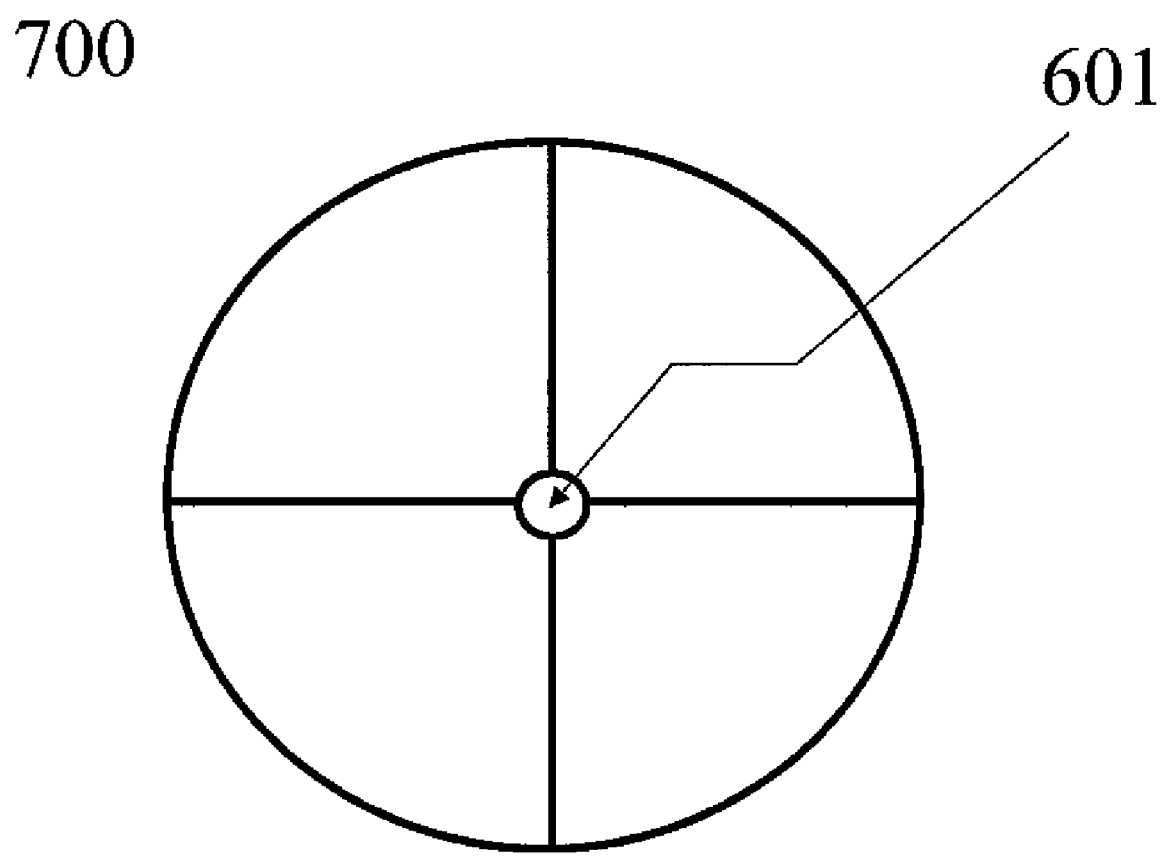
FIG. 7 is a diagrammatic representation of a sample in which a 4 segments detector forms a hole at optical axis.
Figure 8:
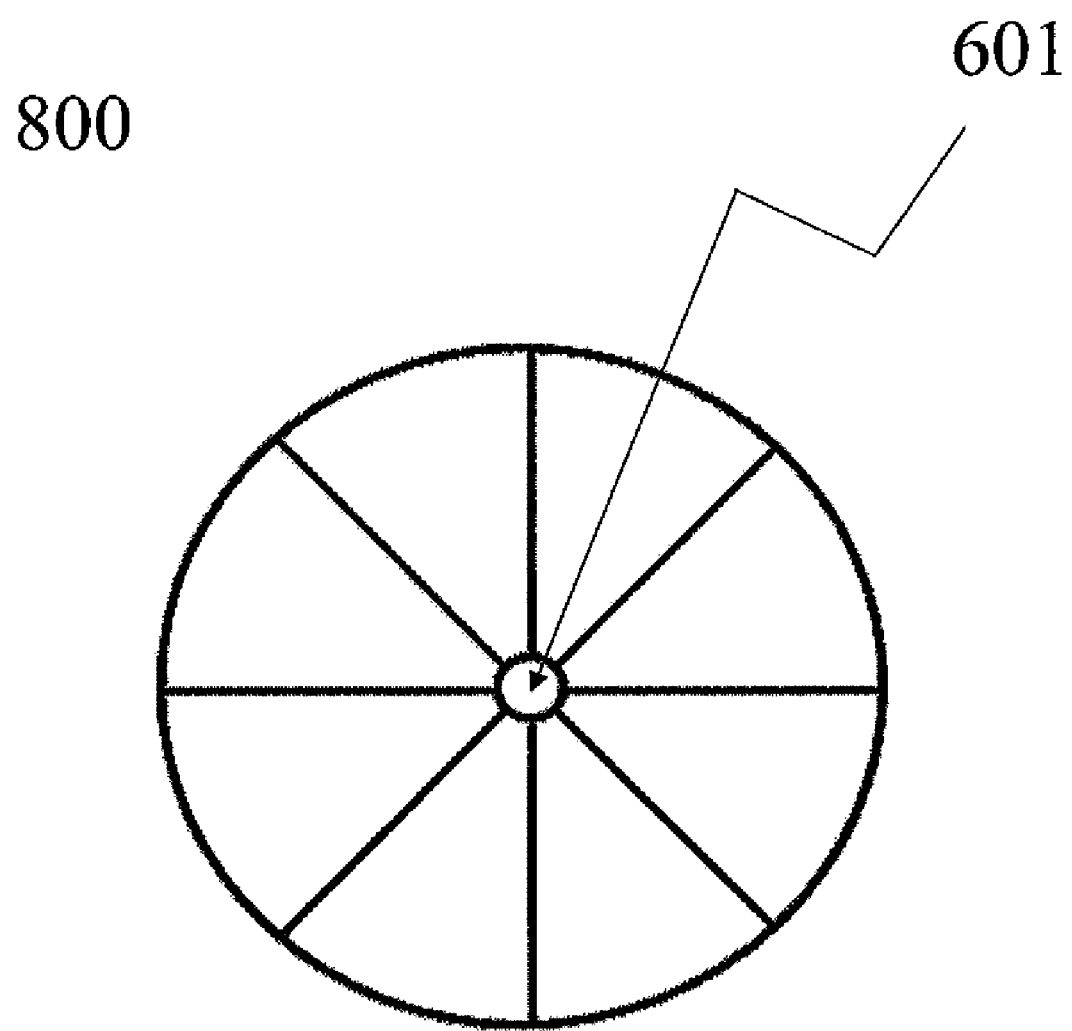
FIG. 8 is a diagrammatic representation of a sample in which an 8 segments detector forms a hole at optical axis.
Figure 9:
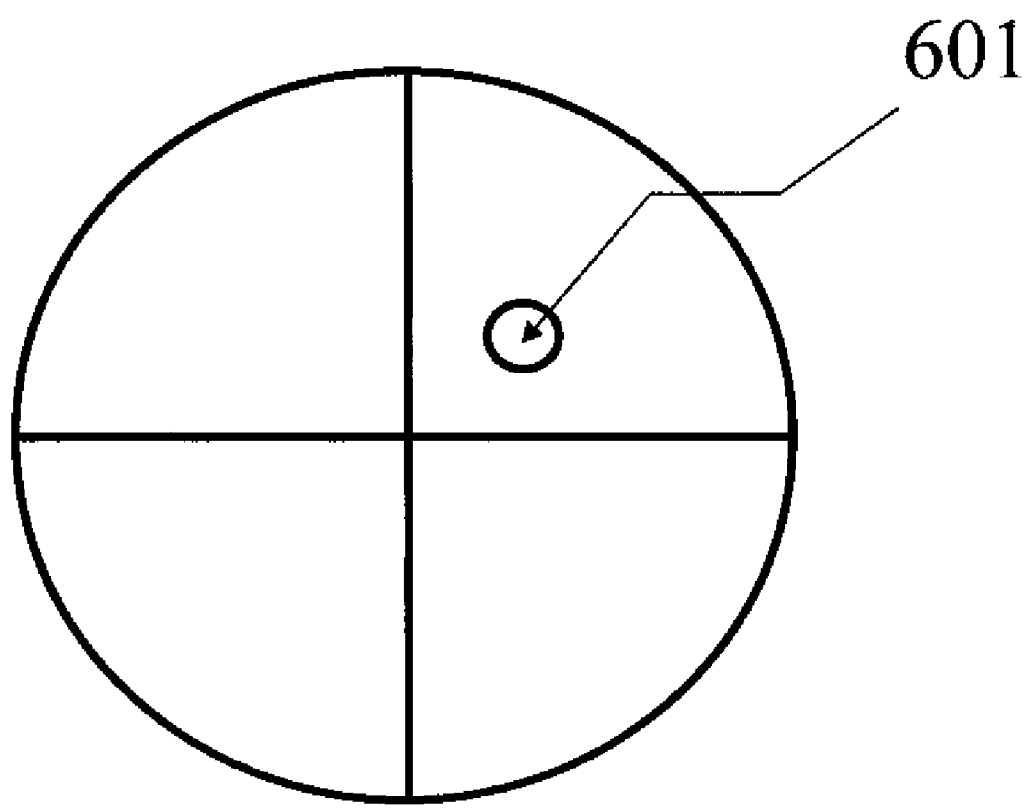
FIG. 9 is a diagrammatic representation of a sample in which one of the detector segments has a hole, which is located at optical axis.
Figure 10:
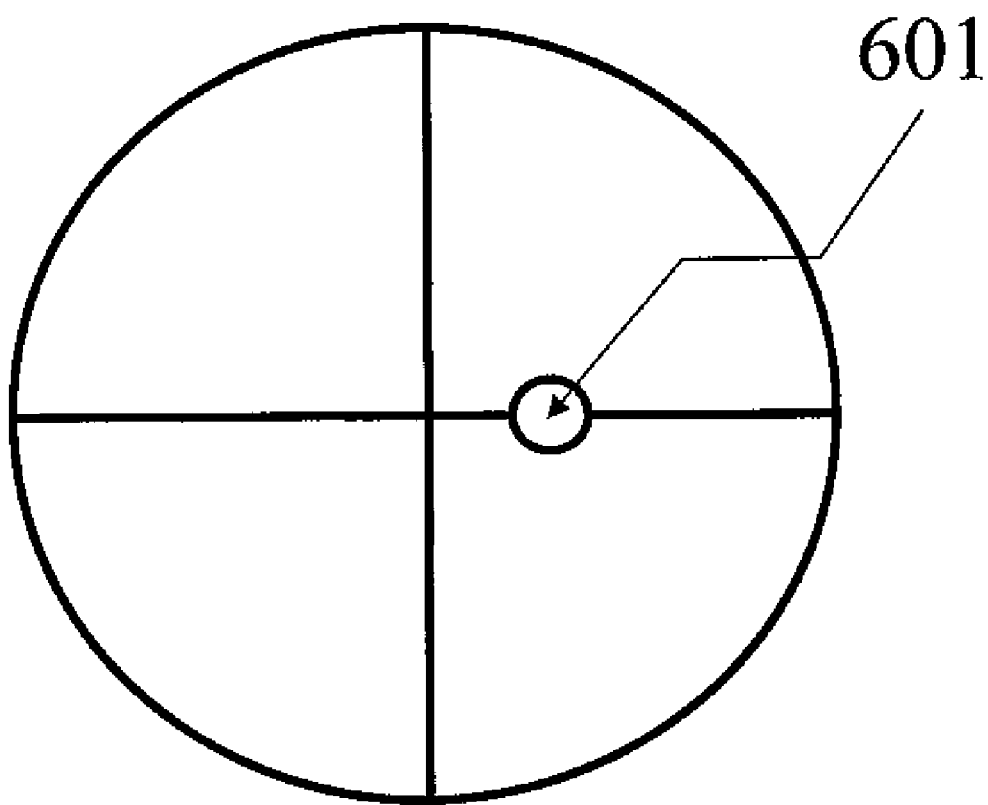
FIG. 10 is a diagrammatic representation of a sample in which some detector segments form a hole, which is located at optical axis center.
Figure 11:
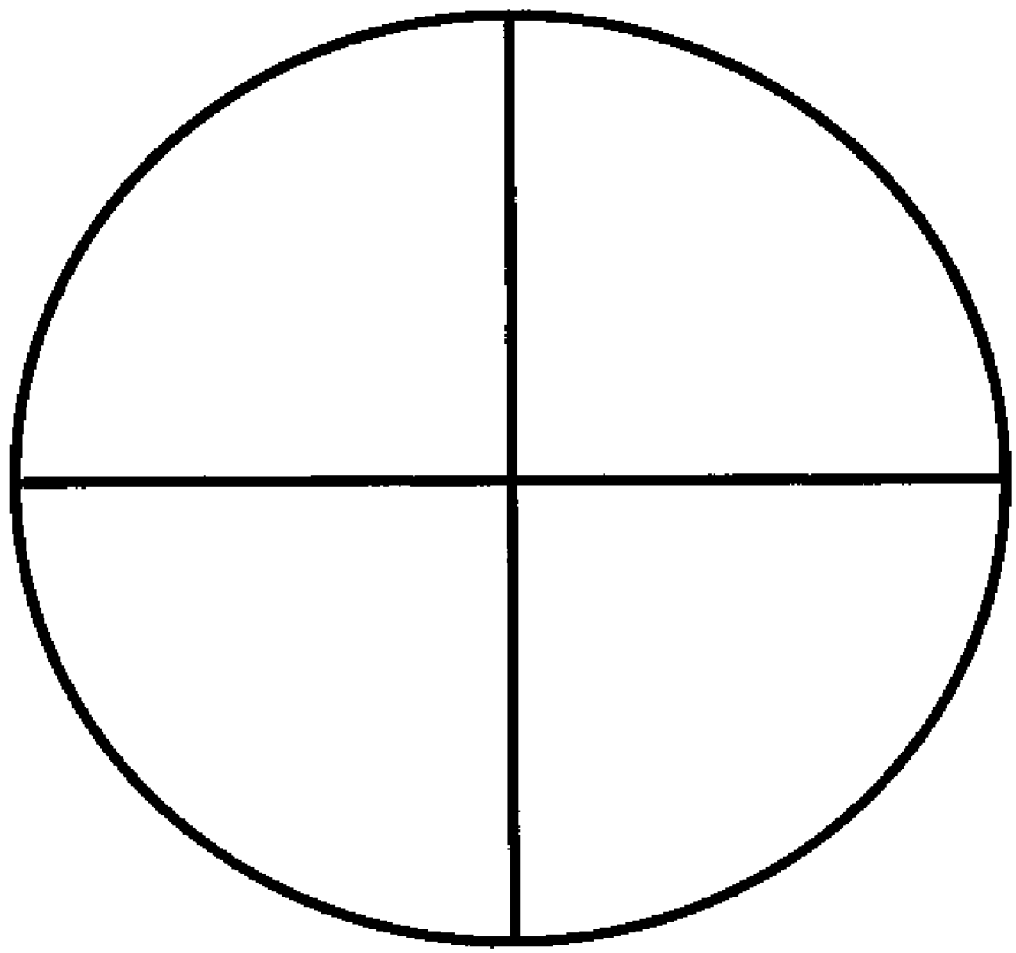
FIG. 11 is a diagrammatic representation of a sample detector that does not locate at the beam optical axis. An ExB filter is utilized to guide the secondary electrons onto the off-axis sectional detector.

FIGS. 6 through FIG. 11 illustrate different sectional detectors samples for SEM image processing. FIG. 6 is a diagrammatic representation of a sample sectional detector with an aperture in the center. FIG. 7 is a diagrammatic representation of a sample in which a 4 segments detector forms a hole at optical axis. FIG. 8 is a diagrammatic representation of a sample in which an 8 segments detector forms a hole at optical axis. FIG. 9 is a diagrammatic representation of a sample in which one of the detector segments has a hole, which is located at optical axis. FIG. 10 is a diagrammatic representation of a sample in which some detector segments form a hole, which is located at optical axis center. FIG. 11 is a diagrammatic representation of a sample detector that does not locate at the beam optical axis. An ExB filter is utilized to guide the secondary electrons onto the off-axis sectional detector.

Figure 5:
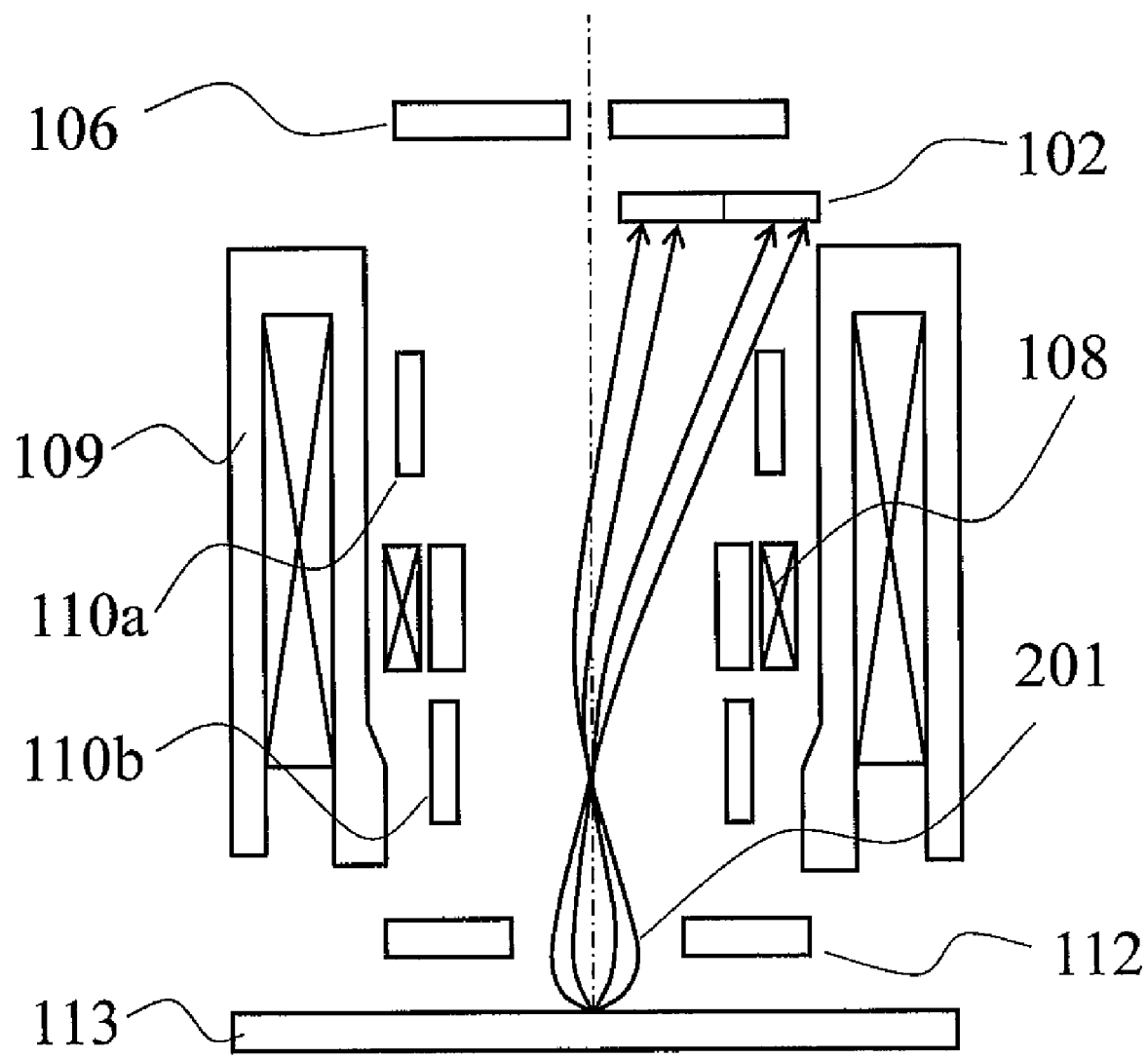
FIG. 5 is a diagrammatic representation of the trajectory of secondary electrons emanating from specimen surface to off-axis sectional detector guided by an ExB filter.

The sectional detector is divided into at least two sections with an aperture in the center 600, 700 and 800. The size of the center aperture 601 is less than 3 mm to let the primary charged particle 102 to pass. The aperture 601 can also be located at section of the sectional detector 900 and between the boundaries of the sections of detector 1000. If the detector is located off-axis of the optical system, the aperture hole can also be removed, shown as 114 in FIG. 11, then the SE emanating from specimen surface 113 is guided to the off-axis sectional detector 114 by an ExB filter 108 as FIG. 5 illustrates.

Each section of the detector collects only the secondary charged particles with particular range of the polar and azimuth angle with respect to the specimen surface 113. The SEM image generated by a particular secondary charge particle is the side-view image, which corresponds to the side-view SEM image collected by a conventional side-detector. The signal from all sections of the sectional detector can be processed to achieve a plane-view SEM image of the scanned specimen area.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

We claim:

1. An electron beam apparatus for collecting side-view and plane-view SEM images, the apparatus comprising:
    an electron source, the electron source providing an electron beam;
    an objective lens, the objective lens for providing a magnetic immersion function and a retarding function, the objective lens for focusing the electron beam onto a sample surface; and
    in-lens detectors, the in-lens detectors comprising two or more segments for receiving secondary electrons emanating from the sample surface, each detector segment collecting the secondary electrons emanating from the specimen with related azimuth and polar angle so that a side-view SEM image can be revealed after a signal processing, wherein one of the two or more segments includes an aperture to let the primary electron pass through.

2. The electron beam apparatus of claim 1 in which each of the in-lens detectors comprises at least two or more segments to collect the secondary electrons emanating from the sample with different azimuth angle, the diameter of the aperture being less than 3 millimeters.

3. The electron beam apparatus of claim 1 in which each of the in-lens detectors comprises at least two or more segments to collect the secondary electrons emanating from the sample with a different azimuth angle, one of the detector segments having a small hole on the optical axis to let primary electron pass through, the diameter of the hole being less than 3 millimeters.

4. The electron beam apparatus of claim 1, in which each of the in-lens detectors comprises at least two or more segments to collect the secondary electrons emanating from the sample with different azimuth angle, some of the detector segments forming a small hole on the optical axis to let primary electron pass through, the diameter of the hole being less than 3 millimeters.

5. The electron beam apparatus of claim 1, in which each of the in-lens detectors comprise at least two or more segments being set near by the optical axis of primary beam to collect the secondary electrons emanating from the sample with different azimuth and polar angle, the secondary electrons emanating from the sample with different azimuth and polar angle being guided to the detector by an ExB filter to form a side-view SEM image without affecting the primary beam.

6. A method for collecting side-view and plane-view SEM images, the apparatus comprising:
   providing an electron beam;
   providing a magnetic immersion function and a retarding function, the objective lens for focusing the electron beam onto a sample surface; and
   providing in-lens detectors, the in-lens detectors comprising two or more segments for receiving secondary electrons emanating from the sample surface, each detector segment collecting the secondary electrons emanating from the specimen with related azimuth and polar angle so that a side-view SEM image can be revealed after a signal processing, wherein one of the two or more segments includes an aperture to let the primary electron pass through.

7. The method of claim 6 in which each of the in-lens detectors comprises at least two or more segments to collect the secondary electrons emanating from the sample with different azimuth angle, the diameter of the aperture being less than 3 millimeters.

8. The method of claim 6 in which each of the in-lens detectors comprises at least two or more segments to collect the secondary electrons emanating from the sample with a different azimuth angle, one of the detector segments having a small hole on the optical axis to let primary electron pass through, the diameter of the hole being less than 3 millimeters.

9. The method of claim 6, in which each of the in-lens detectors comprises at least two or more segments to collect the secondary electrons emanating from the sample with different azimuth angle, some of the detector segments forming a small hole on the optical axis to let primary electron pass through, the diameter of the hole being less than 3 millimeters.

10. The method of claim 6, in which each of the in-lens detectors comprise at least two or more segments being set near by the optical axis of primary beam to collect the secondary electrons emanating from the sample with different azimuth and polar angle, the secondary electrons emanating from the sample with different azimuth and polar angle being guided to the detector by an ExB filter to form a side-view SEM image without affecting the primary beam.

11. An electron beam apparatus for collecting side-view and plane-view SEM images, the apparatus comprising:
   an electron source, the electron source providing an electron beam;
   an objective lens, the objective lens for providing a magnetic immersion function and a retarding function, the objective lens for focusing the electron beam onto a sample surface; and
   in-lens detectors, the in-lens detectors comprising two or more segments for receiving secondary electrons emanating from the sample surface, the segments circling a center wherein the center has no detector, each detector segment collecting the secondary electrons emanating from the specimen with related azimuth and polar angle so that a side-view SEM image can be revealed after a signal processing.

12. The electron beam apparatus of claim 11 in which each of the in-lens detectors comprises at least two or more segments to collect the secondary electrons emanating from the sample with different azimuth angle, the plurality of detector segments forming a small hole on the optical axis to let the primary electron pass through, the diameter of the hole being less than 3 millimeters.

13. The electron beam apparatus of claim 11 in which each of the in-lens detectors comprises at least two or more segments to collect the secondary electrons emanating from the sample with a different azimuth angle, one of the detector segments having a small hole on the optical axis to let primary electron pass through, the diameter of the hole being less than 3 millimeters.

14. The electron beam apparatus of claim 11, in which each of the in-lens detectors comprises at least two or more segments to collect the secondary electrons emanating from the sample with different azimuth angle, some of the detector segments forming a small hole on the optical axis to let primary electron pass through, the diameter of the hole being less than 3 millimeters.

15. The electron beam apparatus of claim 11, in which each of the in-lens detectors comprise at least two or more segments being set near by the optical axis of primary beam to collect the secondary electrons emanating from the sample with different azimuth and polar angle, the secondary electrons emanating from the sample with different azimuth and polar angle being guided to the detector by an ExB filter to form a side-view SEM image without affecting the primary beam.

* * * * *